United States Patent
Rao et al.

(10) Patent No.: US 6,592,911 B2
(45) Date of Patent: Jul. 15, 2003

(54) **(−)-OLIVIL AS ANTIOXIDANT WHICH IS OBTAINED FROM A NEW NATURAL SOURCE NAMELY *STEREOSPERMUM PERSONATUM***

(75) Inventors: Janaswamy Madhusudana Rao, Andhra Pradesh (IN); Ashok Kumar Tiwari, Andhra Pradesh (IN); Upparapalli Sampath Kumar, Andhra Pradesh (IN); Jhillu Singh Yadav, Andhra Pradesh (IN); Kondapuram Vijaya Raghavan, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/917,404

(22) Filed: Jul. 27, 2001

(65) Prior Publication Data

US 2003/0032633 A1 Feb. 13, 2003

(51) Int. Cl.[7] ............................................. A61K 35/78

(52) U.S. Cl. ..................................... 424/769; 424/725
(58) Field of Search ............................... 424/725, 769

(56) References Cited

PUBLICATIONS

Ghogomu–Tin, R. et al.,,, Isolation and Identification of (−)–Olivil and (+)–Cycloolivil from *Stereospermum kunthianum*, 1985, Planta Medica, No. 5, 464.*

Ghogomu–Tin, R. et al.,,, Chemical Constituents of the Stem Heart Wood of *Stereospermum kunthianum*, 1986, Planta Medica, No. 4, 342.*

* cited by examiner

*Primary Examiner*—Christopher R. Tate
*Assistant Examiner*—Kailash C. Srivastava
(74) *Attorney, Agent, or Firm*—Merchant & Gould P.C.

(57) ABSTRACT

This invention relates to a pharmaceutical composition comprising an effective amount of (−)-Olivil together with or associated with an additive useful as an antioxidant; a process for isolating the (−)-Olivil from the pant *Stereospermum personatum* and also relates to use of the active fraction (−)-Olivil as an antioxidant or free radical scavenger.

2 Claims, 1 Drawing Sheet

Figure 1:
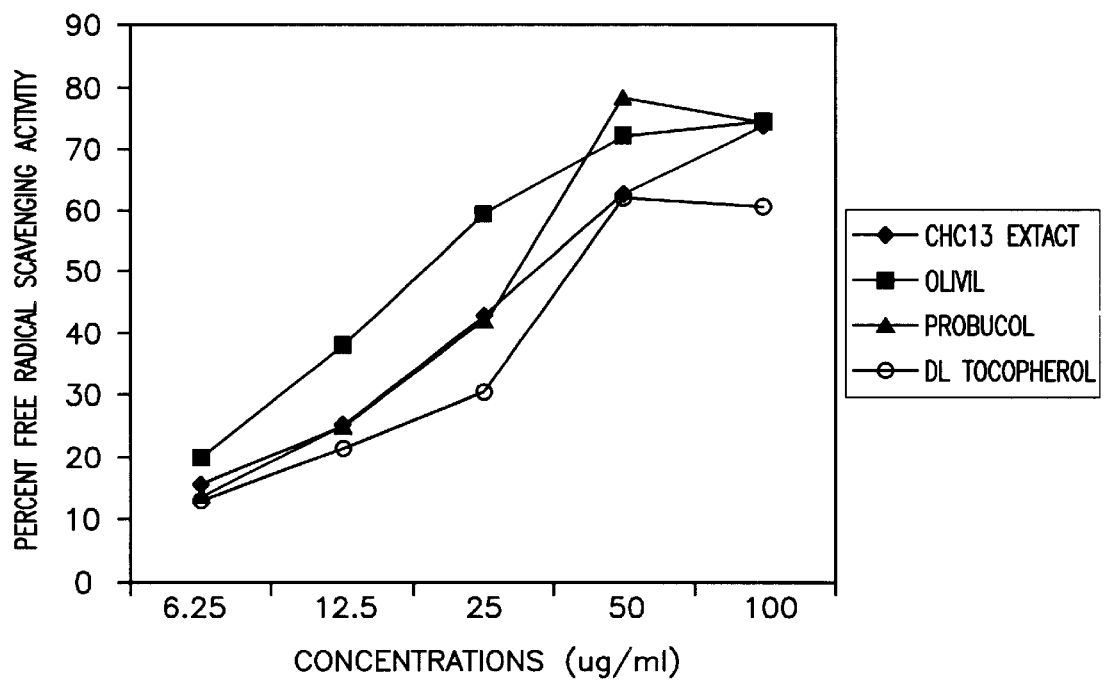

ANTIOXIDANT (ANTI-FREE RADICAL, DPPH) ACTIVITY OF OLIVIL FROM S. PERSONATUM AND REFERENCE COMPOUNDS (−)−OLIVIL

(−)-OLIVIL AS ANTIOXIDANT WHICH IS OBTAINED FROM A NEW NATURAL SOURCE NAMELY *STEREOSPERMUM PERSONATUM*

FIELD OF THE INVENTION

This invention relates to the isolation of compound namely (−)-Olivil from a new plant source, *Stereospermum personatum* in good yield. It is proved to be useful and better antioxidant molecule than the presently used medicinally important lipophilic antioxidants Prubucol and α-Tocopherol. It may have better therapeutic potential in inflammatory disease conditions, atherosclerosis, diabetic complications, cancer, hepatotoxicity and variety of disease conditions mediated through or fostered by oxidative stress and/or overt oxidative burden due to increased generation or under scavenging of free radicals.

BACKGROUND AND PRIOR ART REFERENCES

There is a considerable amount of epidemiological evidence indicating association between diet rich in fruits and vegetables and a decreased risk of cardiovascular disease and certain forms of cancer. It is generally assumed that the active principles contributing to these protective effects are nothing but primarily, the antioxidant phytochemicals.

Research in the past decades have accumulated enough evidence to show the beneficial effect of free-radical scanvengers/antioxidants as antimutagenic, antinflammatory, antiamerosclerotic, antidiabetic, antihepatotoxic, antiageing and in a variety of neurological disorders. The search for new antioxidant principles is becoming therefore, essential to improve the pharmacological treatment of pathalogical conditions related either due to free radical/oxidative damage or due to imbalance between antioxidant/oxidant homeostasis such as cataract, rheumatic diseases, atherosclerosis, Alzheimer's disease and other neurodegenarative conditions.

The pharmacological approaches therefore have focused on the search of potential resources rich in antioxidant principles. The medicinal importance of plants bearing rich proportion of antioxidant principles is therefore becoming hot item.

*Stereospermum personatum* is a medicinal plant used in traditional Indian System of Medicine and is widely advocated in the preparations for diuretic, lithontriptic, expectorant, cardiotonic, aphrodisiac, appetizer, antiinflammatory, antibacterial dyspepsia, diarrhea, renal and vesical calculi, cough, asthma, hyperdipsia, haemorrhoids and hyperacidity disease conditions( Indian Medicinal Plants, Vol 5 p 192). It is further reported to possess antibacterial, antifungal, hypoglycaemic activity, and against p388 lymphocytic leukemic cells (Ind. Jour, of Exp. Biol., 1971,9, 100). Hence, it becomes pertinent to look for the molecules possessing such important biological properties. In this connection, the phytochemical investigation of *Stereospermum personatum* has been taken up. The applicants made efforts to the isolation of (−)-Olivil in good yield.

(−)-Olivil is known to possess several activities, which are shown in Table.1

TABLE 1

| Compound | Activity | Reference |
| --- | --- | --- |
| (−)-Olivil | 1. Cyclic AMP phosphodiesterase inhibition | Chem. Pharm. Bull, 1981, 29, 3586–92 |

TABLE 1-continued

| Compound | Activity | Reference |
| --- | --- | --- |
| | 2. Antihypertensive and $Ca^{2+}$ antagonist activity | Chem. Pharm. Bull, 1986, 34, 3514–17 |
| | 3. Inhibition of adenosine 3' 5' cyclic monophosphate phosphodiesterase | Chem. Pharm. Bull. 1988, 36, 435–9 |
| | 4. Inhibition of ethanol addiction | UK Pat. No. GB 2,198,041 |
| | 5. Anti complementary activity, antagonist activity | J. Ethanopharmacology, 1988, 23, 159 |

OBJECTS OF THE INVENTION

The main object of the invention is to provide a novel composition containing (−)-Olivil and an additive, which is used as an antioxidant.

Another object is to provide a new source for obtaining (−)-Olivil in good yield.

Yet another object of the invention is to provide a process for producing (−)-Olivil from a plant source namely *Stereospermum personatum*.

Yet another object of the invention is relates to use of (−)-Olivil as an antioxidant.

SUMMARY OF INVENTION

Accordingly, the invention provides a novel composition containing (−)-Olivil and useful as antioxidant. The invention further provides a method for the isolation of (−)-Olivil from a new plant source namely *Stereospermum personatum*.

In accordance with this invention, it has been found that (−)-Olivil is isolated from a new source, *Stereospermum personatum* in significant yield and it has been found that (−)-Olivil show antioxidant property.

DETAILED DESCRIPTION OF THE INVENTION

Antioxidant compounds recently have attracted the attention due to their broad spectrum of activities in disorders of multiple origin viz., coronary heart disease, cancer, diabetes, rheumatic disorders and inflammatory conditions where free radicals play important role. Much attention is being directed now to harness and harvest the antioxidant compounds from natural resources.

The compound (−)-Olivil is used in pure form. Hence, the usage may be more advantageous than a mixture of compounds having similar properties, which are in current use. It is also important to note that the process of isolation of (−)-Olivil is highly economical.

The present invention provides a useful source, *Stereospermum personatum*, comprising antioxidant principle of which (−)-Olivil is isolated as pure and potent antioxidant molecule. (−)-Olivil has been compared with existing pharmacologically/therapeutically accepted antioxidant Probucol and alpha-tocopherol. It is found that (−)-Olivil is better than the above mentioned reference drugs and hence may be used with pharmaceutically/therapeutically acceptable additives.

In an embodiment of the present invention, (−)-Olivil may be effective in much less amount than the reference drugs mentioned above.

One embodiment of the present invention relates to a composition useful as antioxidant, said composition comprising an effective amount of (−)-Olivil in combination with or associated with a pharmaceutically acceptable additives.

In another embodiment of the invention, the pharmaceutically acceptable additive is selected in such a manner that it does not affect or interfere with the efficacy of (−)-Olivil.

In still another embodiment of the invention, the additive is selected from nutrients such as carbohydrates, sugar, proteins, fats and pharmaceutically acceptable carrier.

In an embodiment of the present invention, the ratio of (−)-Olivil to the additive is in the range between 0.1:10 to 3:10, preferably 0.4:10 to 2:10.

In yet another embodiment of the invention, the amount of (−)-Olivil administered is in the range between 300 mg to 400 mg per dose at least twice a day In yet another embodiment of the invention, the composition is administered through oral route in the form of tablets, capsules, syrup or powder.

One more embodiment of the invention relates to a process for isolation of (−)-Olivil from the plant *Stereospermum personatum* said process comprising the steps of:

a) extracting a dried wood powder of *Stereospermum personatum* with hexane;

b) further extracting a residue from step (a) with chloroform;

c) concentrating the chloroform solution from step (b) under vacuum;

d) absorbing a dark brown extract on a silicagel (60–120 mesh) and loaded on a silicagel (60–120 mesh) column (4 cm dia to height of 100 cm);

e) eluting die column wit chloroform methanol gradient, and f) collecting an eluted fraction wit 4% methanol in chloroform and concentrating the fraction to obtain pure (−)-Olivil.

In another embodiment of the present invention, solvents used are selected from the group of hexane, chloroform and methanol.

In another embodiment of the present invention, a yield of (−)-Olivil obtained is about 0.073% of a dried plant material.

One more embodiment relates to use of (−)-Olivil as an antioxidant or free-radical scavenger for animals and human beings.

In yet another embodiment relates to use of (−)-Olivil for the manufacturing of a composition useful as an antioxidant.

In yet another embodiment of the present invention, (−)-Olivil is administered orally.

Yet another embodiment of the invention relates to a method for the treatment of free radical scavenging, comprising the steps of administration of an effective amount of (−)-Olivil to a subject in need thereof preferably, (−)-Olivil is administered in the range of 300 mg–400 mg/dose, twice a day.

*Stereospermum personatum* hence is a new source for (−)-Olivil and its presence in this plant in good yields makes this invention more important. A comparison of yield (−)-Olivil from different plants is given in Table 2.

TABLE 2

| Name of the plant | % yield of (−)-Olivil | Reference |
|---|---|---|
| *Olea europaea* | 0.0015 | Chem. Pharm. Bull. 1984, 32, 2730 |
| *Eucommia ulmoides* | 0.002 | Chem. Pharm. Bull. 1986, 34, 523 |

TABLE 2-continued

| Name of the plant | % yield of (−)-Olivil | Reference |
|---|---|---|
| *Stereospermum kunthianum* | 0.0012 | Plant. Med. 1986 |
| *Stereospermum personatum* | 0.073 | Present invention |

The present invention embodies isolation of (−)-Olivil, as antioxidant principle from a new plant source and identify its free radical scavenging property compared with medicinally important antioxidant drug molecules.

BRIEF DESCRIPTION OF THE ACCOMPANYING DRAWING

Figure 2:
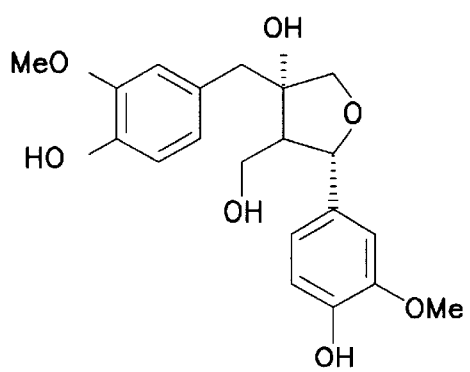

FIG. 1 shows antioxidant (Anti-free radical, DPPH) activity of (−)-Olivil from *Stereospermum personatum* and reference compounds FIG. 2 represents the structure of (−)-Olivil.

The invention is further described in the following examples that are given by the way of illustration and therefore should not be construed to limit the invention in any manner.

EXAMPLE 1

Experimental protocol: A process for the isolation of a lignan as above. A dried wood powder of *Stereospermum personatum* (3 Kg) was loaded on a Soxhlet apparatus. The powder was first extracted with hexane. A residue from the extraction of hexane was further extracted with chloroform. The chloroform solution was concentrated under vacuum. A dark brown extract (22 g) was adsorbed on a silica gel (60–120 mesh) and loaded on a silica gel (60–120 mesh) column (4 cm diameter tea height of 100 cm).

The column is subjected to elution with chloroform methanol gradient. The chloroform-methanol gradient is so selected to obtain specific fraction and thereby the desired compound. In the present case, the fractions eluted at 4% methanol in chloroform are collected separately and concentrated.

The above fractions are subjected to further purification using silica gel column (>200 mesh, 2.5 cm dia and 50 cm length) using chloroform methanol gradient. The eluent at 4% methanol in chloroform gave pure (−)-Olivil (2.2 g). The spectrochemical data of (−)-Olivil are given below:

(−)-Olivil

1. Molecular formula: $C_{20}H_{24}O_7$
2. $^1$HNMR: δ 2.45(1H, m), 2.9(1 H, d), 3.05(1H, d), 3.65 (1H, d), 3.95–3.80(3H, m), 3.85(6H, s), 4.7(1H, d), 5.6 (Ar—OH, s), 5.65(Ar—OH, s), 6.75–6.90(5H, m), 7.1 (1H, s).
3. $^{13}$CNMR: δ 39.19(C-7'), 55.80(2×OCH$_3$), 59.42(C-8'), 59.91(C-9), 77.79(C-9'), 81.18(C-8'), 83.64(C-7), 109.60 (C-2'), 113.50(C-2), 114.46(C-5,),1I4.60(C-5), 119(C-6,), I22.83(C-6), 128.56(C-1),133.64(C-1'), 144.56(C-4,), 145.47(C-4), 146.82(c-3'), 147.18(C-3).
4. MS: 376(M$^+$)
5. IR: 3401 cm$^{-1}$

EXAMPLE 2

In Vitro Evaluation of Free Radical Scavenging Antioxidant Potency

Antioxidant activity of the compounds was tested for its capacity/potency to scavenge most widely used free radical, 1,1-diphenyl-2-picryl hyrazyl radical (DPPH). The well-accepted and tested antioxidants namely probucol and α-tocopherol were taken as reference compounds. 1 mg/ml DMSO concentration of the compounds were prepared and subsequently, diluted to lower concentrations with DMSO. 200 μl of test compounds were reconstituted to 1 ml in tris-HCl buffer (pH 7.4). Equal volume of 500 μM of DPPH radical dissolved in ethanol was reacted with this. After incubation for 45 minutes in dark, the absorbency at 517 nm was recorded. Percent radical scavenging activity was calculated accordingly. All the readings were taken in triplicate. Results (FIG. 1 and Table 3) shows that compound under consideration possess potent antioxidant/free-radical scavenging property.

TABLE 3

50% Radical scavenging concentration of compounds

| Antioxidant | Concentration (μg/ml) |
|---|---|
| CHCl$_3$ Extract | 40.09 |
| (−)-Olivil | 22.24 |
| Probucol | 28.71 |
| DL α-Tocopherol | 47.80 |

What is claimed is:

1. A process for isolation of (−)-Olivil from the plant *Stereospermum personatum*, said process comprising the steps of:
   a) extracting dried wood powder of the plant *Stereospermum personatum* with hexane to obtain a hexane extract and a plant residue;
   b) extracting the plant residue from step (a) with chloroform to obtain a chloroform extract;
   c) concentrating the chloroform extract from step (b) under reduced pressure to obtain a dark brown residue;
   d) absorbing the dark brown residue of step (c) on a silicagel of particle size 60–120 mesh and putting the silica gel on a silica gel column;
   e) eluting a fraction from the column of step (d) with a mixture of chloroform-methanol gradient, the mixture of chloroform-methanol gradient comprising 4% methanol, and
   f) collecting the fraction eluted from step (e) and concentrating the fraction to obtain pure (−)-Olivil.

2. A process as claimed in claim 1 wherein, a yield of (−)-Olivil obtained is about 0.073 percent by weight of a dried plant material of the plant *Stereospermum personatum*.

* * * * *